(12) United States Patent
Thompson et al.

(10) Patent No.: US 10,028,490 B2
(45) Date of Patent: Jul. 24, 2018

(54) COMPREHENSIVE POULTRY MANURE MANAGEMENT METHOD

(71) Applicant: Poultry EcoServices, LLC, Annapolis, MD (US)

(72) Inventors: Patrick Clark Thompson, Arnold, MD (US); Rafael Sepulveda Correa, Salisbury, MD (US)

(73) Assignee: Poultry EcoServices, LLC, Annapolis, MD (US)

( * ) Notice: Subject to any disclaimer, the term of this patent is extended or adjusted under 35 U.S.C. 154(b) by 0 days.

(21) Appl. No.: 15/484,230

(22) Filed: Apr. 11, 2017

(65) Prior Publication Data
US 2017/0290304 A1   Oct. 12, 2017

Related U.S. Application Data

(60) Provisional application No. 62/321,431, filed on Apr. 12, 2016.

(51) Int. Cl.
| | |
|---|---|
| *A01K 31/18* | (2006.01) |
| *A01K 31/20* | (2006.01) |
| *A61L 2/20* | (2006.01) |
| *A01K 1/01* | (2006.01) |

(52) U.S. Cl.
CPC ............ *A01K 31/20* (2013.01); *A01K 1/0103* (2013.01); *A61L 2/202* (2013.01)

(58) Field of Classification Search
CPC .... A01K 31/005; A01K 31/007; A01K 31/18; A01K 31/22; A01K 31/04; A01K 1/0047; A01K 1/01; A01K 13/003; A61L 2/202
USPC ....... 119/436, 437, 444, 447, 448, 450, 420, 119/525–530, 534; 422/29, 28, 4, 5, 422/186.07
See application file for complete search history.

(56) References Cited

U.S. PATENT DOCUMENTS

| | | | | |
|---|---|---|---|---|
| 3,396,703 A | * | 8/1968 | Trussell | A01K 31/005 119/301 |
| 6,156,268 A | * | 12/2000 | Curry | A61L 9/015 422/129 |
| 6,276,304 B1 | * | 8/2001 | Tai | A01K 1/0047 119/448 |
| 6,325,971 B1 | * | 12/2001 | Hayes | A01K 1/0047 119/437 |
| 8,132,535 B2 | | 3/2012 | Correa | |
| 2004/0141874 A1 | * | 7/2004 | Mullinax | A61L 2/202 422/4 |

(Continued)

*Primary Examiner* — Trinh T Nguyen
(74) *Attorney, Agent, or Firm* — Laubscher, Spendlove & Laubscher, P.C.

(57) ABSTRACT

An integrated system of technology applications and methods to provide comprehensive management of poultry waste improves the productivity of poultry housing facilities while reducing the environmental and public health impacts of poultry production. The method utilizes a plurality of housing units, each including plenum flooring and ventilation to improve the health of birds as they grow from hatchlings to market size adults. After the birds are removed from the housing units, manure is immediately removed from the flooring system and preferably transported to a processing facility. The units are cleaned and fumigated with ozone so that they are ready to receive a new flock within approximately 48 hours from removal of the preceding flock.

5 Claims, 2 Drawing Sheets

(56) References Cited

U.S. PATENT DOCUMENTS

| | | | | |
|---|---|---|---|---|
| 2007/0006815 A1* | 1/2007 | Correa | ................ | A01K 1/0029 |
| | | | | 119/443 |
| 2009/0301402 A1* | 12/2009 | Devine | ................... | A01K 1/00 |
| | | | | 119/447 |
| 2011/0061601 A1* | 3/2011 | Correa | ................ | A01K 1/0029 |
| | | | | 119/437 |
| 2012/0055414 A1* | 3/2012 | Correa | ................ | A01K 1/0029 |
| | | | | 119/448 |

* cited by examiner

COMPREHENSIVE POULTRY MANURE MANAGEMENT METHOD

This application claims the benefit of U.S. provisional patent application No. 62/321,431 filed Apr. 12, 2016.

BACKGROUND OF THE INVENTION

The present invention is in the technical field of agricultural food animal production. More particularly, the invention relates to poultry waste management and, specifically, to fumigation of a commercial poultry housing unit that is equipped with a ventilated plenum flooring system. A properly installed and operated ventilated plenum flooring system eliminates the need for bedding material and facilitates manure removal immediately after collection of each market ready flock. However, widely accepted industry practice requires at least fourteen full days of "layout time" to lower airborne ammonia concentrations and reduce housing unit microbial pathogens through fresh air ventilation for an extended period before a poultry housing unit is restocked with a new poultry flock. Conventional practice overlooks the potential benefits of a ventilated flooring system with just-in-time manure cleanout and fumigation after each flock, virtually eliminating ammonia and achieving managed reduction of pathogens within a brief time interval. The reduction of flock cycle time through just-in-time manure removal and managed pathogen reduction allows increased operational efficiency while also reducing adverse environmental, public nuisance and potential health impact from commercial meat poultry production.

SUMMARY OF THE INVENTION

The present invention is an integrated system of technology applications and methods to provide comprehensive management of poultry waste (manure), thereby increasing the productivity of poultry housing facilities and improving animal welfare while reducing adverse environmental impact, operational biosecurity risks and public health risks. Although detailed descriptions contained herein are, in some cases, specific to chickens, the concepts also apply to turkeys and other meat poultry species.

Plenum flooring systems are permanently installed in poultry housing units to improve internal environmental conditions without the need for bedding materials, chemical poultry litter treatment (PLT), or high volume dilution air ventilation. Plenum flooring systems improve environmental quality within a housing unit by controlling manure moisture without the need for absorbent bedding materials. Low moisture and absence of carbonaceous bedding material inhibit the biochemical formation and release of ammonia and other harmful gases. Effective control of manure moisture results in a dry, friable matter surface for bird comfort and safety. A high standard of environmental quality within housing units is beneficial to the health and welfare of the birds, allowing growth and development at or near the full genetic potential of the species and minimizing incidence of mortality from environment-related physical and biological challenges. Maintaining environmental quality within housing units also improves local outdoor air quality and reduces nuisance to neighbors by reducing flies, ammonia, dust and odors. These environmental improvements also reduce operational biosecurity risks of avian influenza and other vector- and air-borne pathogens that may accumulate during conventional manure management practices.

Once birds have grown to their target market weight, they are collected and removed from the housing units. Within the same day, manure is also collected and removed from the housing units. The housing units are then fumigated by flooding the interior space with a dry air-ozone ($O_3$) mixture, produced by one or more onsite or mobile ozone generator units. Ozone generator capacity is sized to achieve and maintain an ozone concentration for effective destruction of target pathogens, insects and fungi. The ozone generator units are equipped with timing devices to automatically stop ozone production after a pre-set run time and provide a "safe entry" signal after a programmed delay to allow natural decomposition of ozone to safe and stable diatomic oxygen (O2). The fumigation process reduces biological challenges to bird health and lowers the spread of pathogens throughout the poultry transportation and processing supply chain and to the general public through worker contamination and poultry housing unit ventilation exhaust. Reduction of insects such as flies reduces operational biosecurity risks such as pathogenic avian influenza.

Generally, the inventive process includes installing plenum flooring, making poultry housing unit modifications and implementing methods for the generation and distribution of ozone within poultry housing units. By controlling ozone concentrations and exposure duration, the fumigation method provides managed reduction of pathogens, allowing reduced flock cycle time, lower mortality rates, reduced operational biosecurity risk, improved animal welfare and reduced public nuisance and health risk.

BRIEF DESCRIPTION OF THE FIGURES

Other objects and advantages of the invention will become apparent from a study of the following drawing when viewed in the light of the accompanying drawing, in which.

DETAILED DESCRIPTION

Commercial production of meat poultry is generally performed in large housing units that are designed to protect birds from external threats such as predators and harsh weather conditions and to facilitate uniform delivery of nutrition to large flocks. In most cases, the birds are confined within the housing unit throughout their development from hatchlings to market weight adult birds. During this confinement, a bed of manure accumulates on the floor of each housing unit.

Figure 1:
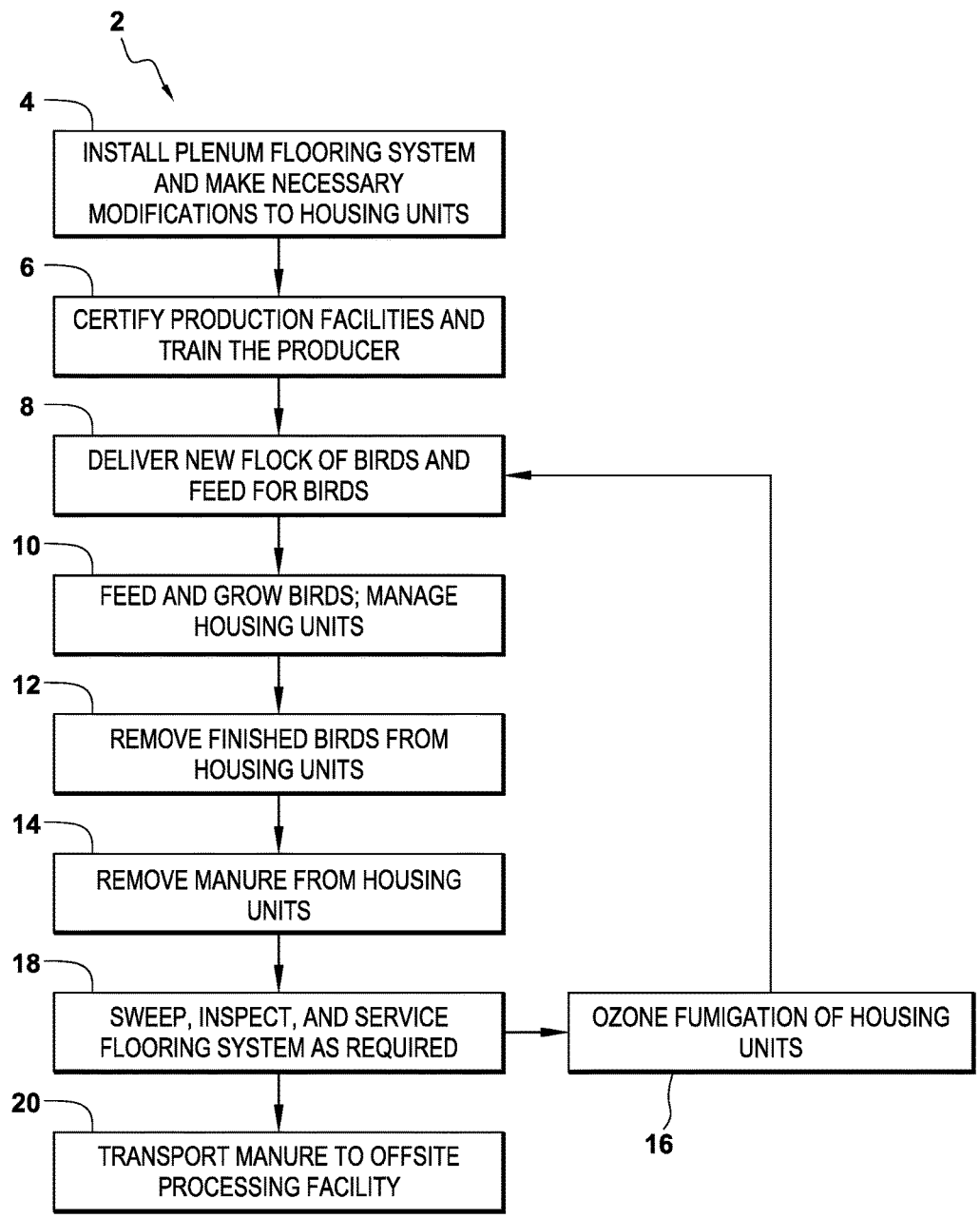
FIG. 1 is a flow chart of the method according to the invention.

Referring now to FIG. 1, the steps for poultry production and waste management 2 will be described. Plenum flooring and ventilation systems are installed 4 within large poultry housing units, and additional modifications to the units are made so that the flooring and ventilation systems will function properly. Each housing unit is divided into segments. The segments are preferably approximately one hundred feet long. At the geometric center of each segment, a reversible ventilation fan is installed. The flooring ventilation fan is sized and configured to regulate flooring temperature and evacuate moisture from the flooring plenum space. Once the flooring and ventilation systems and associated modifications are installed in the housing units, the production facilities are preferably certified 6 according to the protocols within the meat poultry industry. The grower or producer is also preferably trained 6 to perform proper operation and maintenance of the flooring and ventilation systems.

Following certification of installation and producer training, flocks of birds and feed are delivered 8 to the housing units. The birds are fed 10, and the housing units are serviced and maintained. Once the birds have reached their target market weight, they are removed 12 from the housing units. Following bird removal, mobile equipment is used to remove all manure from the housing units 14 and loaded onto trucks.

Once the manure is removed and the flooring system is swept, inspected and serviced as required, targeted fumigation of the flooring plenum space is performed with a sufficient concentration of ozone 16 that substantially eradicates pathogens, insects and fungi to further prepare the housing units for a new flock. Manure is preferably transported 18 to an offsite manure processing facility, eliminating the need for storage or disbursement of the manure at the housing facility site. After fumigation with a programmed delay for ozone decomposition, a new flock of birds is placed in each housing unit 8 and the feeding and grow out production process is repeated.

Figure 2:
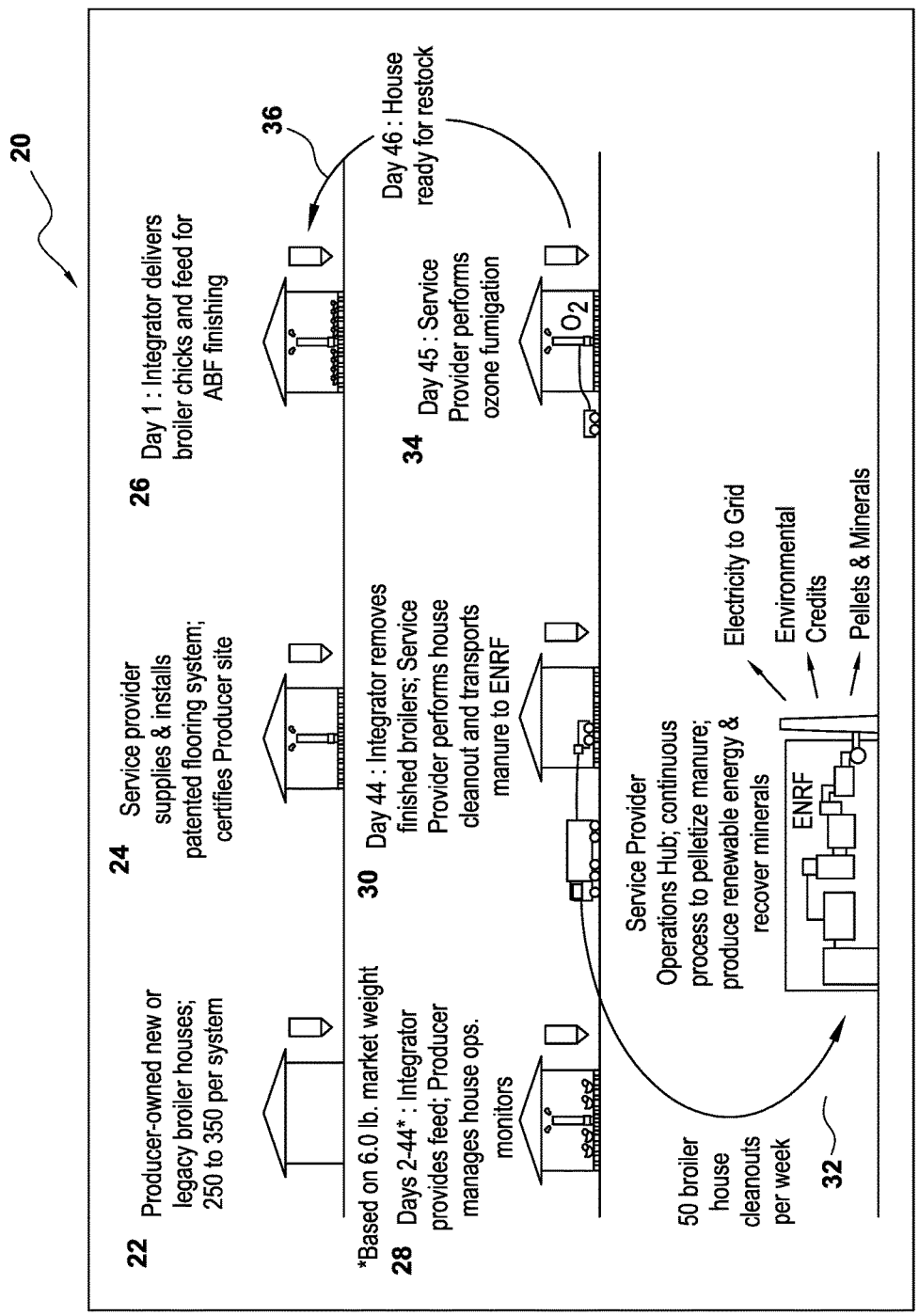
FIG. 2 is a schematic illustration of a preferred embodiment of the comprehensive poultry waste management system.

Referring now to FIG. 2, the comprehensive poultry waste management system 20 according to the invention will be described. The system preferably may include approximately 250 to 350 producer-owned, new or legacy poultry or broiler housing units 22.

A modular plenum flooring system with associated ventilation systems and other modifications is installed 24 in each housing unit, and the poultry producer is trained and certified for proper operation and maintenance of the modified housing features. The flooring system is a ventilated plenum system such as that disclosed in U.S. Pat. No. 8,132,535. A properly installed ventilated plenum flooring system eliminates the need for bedding materials, use of chemical poultry litter treatment (PLT) and use of high volume dilution air ventilation to maintain air quality conditions necessary to achieve the genetic growth potential of commercial meat poultry species. Removal of manure after each poultry flock is known to provide animal welfare as well as productivity benefits for poultry producers. The well managed poultry production facilities with plenum flooring systems in accordance with the subject invention can accomplish this on a just-in-time basis, immediately after each flock removal.

As housing facility plenum flooring and ventilation system installations are completed, poultry hatchlings 26 are delivered each unit. The birds are grown to a pre-defined market weight (usually 3.0 to 8.5 lbs) under the care of the producer. Due to the high-quality environment of the modified housing facility, the integrator will normally implement an antibiotic free (ABF) feeding and growth regimen.

The flock grows to market weight 28. During this period, feed is provided to the birds, and the producer manages the housing facility operations.

Once the target market weight is achieved, the mature birds 30 are removed from the housing units. A waste management service provider performs housing unit cleanout, preferably on the same day as the birds are removed. More particularly, mobile equipment is used to remove all manure from the housing units. The manure is preferably transported to an offsite processing facility 32.

After manure is removed from the housing units and the flooring system is swept, inspected and serviced, each housing unit flooring plenum space is fumigated with a mixture of dry air and ozone ($O_3$) 34 to complete preparations for receiving a new flock 36. Due to its oxidation potential, a high concentration of ozone is effective in destroying pathogens, fungi, insects and their larvae within a brief exposure period. Since the ozone molecule is unstable and quickly decomposes into diatomic oxygen ($O_2$), ozone fumigation enables restocking of a housing unit within minimal time after flock removal. Rapid restocking of a housing unit reduces overall flock cycle time, allowing a poultry producer to maximize housing unit annual production while also reducing mortality rates, improving animal welfare, reducing operational biosecurity risks (by eliminating flies and other insects) and lowering pathogen related risks to public safety. Using "just-in-time" management practices as described above, the flock cycle time, i.e. the time from when the birds are introduced into the housing units to when the birds reach market weight and the housing units are serviced to receive a new flock of birds, is reduced by approximately 12 or more days when compared to the typical flock cycle time with conventional manure management methods.

As noted above, the plenum flooring system is of a specialized type known in the art. It is constructed of non-corrosive and non-biodegradable materials and is designed and installed to ensure sufficient rigidity and durability to withstand repeated live loads of heavy mobile equipment commonly used for poultry house manure cleanout. The plenum flooring ventilation system is configured to operate in coordination with customary poultry house heating and ventilation systems.

The ozone fumigation method improves poultry production economics by reducing poultry flock cycle time. Managed reduction of pathogens, insects and fungi within poultry housing units reduces biological challenges to bird health, thereby lowering mortality rates and improving overall animal welfare and, ultimately, improving producer performance under an antibiotic-free feeding and growth regimen. Managed reduction of poultry housing unit pathogens, insects and fungi also reduces operational biosecurity risks and public health risks associated with the spread of pathogens through ventilation exhaust and worker contact within the community. In addition, improved poultry house productivity allows greater flexibility for capacity expansion in geographic areas with high density poultry production. These improvements enable poultry producers and other poultry meat supply chain participants to achieve higher profitability through reduced costs, increased efficiencies, improved poultry product quality and improved response to consumer demand for antibiotic free food production while also lowering operational biosecurity risks, improving animal welfare and reducing public nuisance and safety concerns.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

What is claimed is:

1. A method for comprehensive poultry manure management, comprising the steps of (a) installing plenum flooring and ventilation systems in at least one poultry housing unit for feeding and growing a flock of meat poultry birds;

(b) cleaning manure from said housing units on the same day that the flock of birds is remove from the housing units after the flock has reached its market weight; and (c) fumigating the housing units with ozone to reduce pathogens, insects and fungi right after the poultry manure is removed, whereupon said housing units are available to receive a new flock of birds.

2. A method as defined in claim 1, wherein the plenum flooring system is formed of non-corrosive and non-biodegradable materials.

3. A method as defined in claim 2, wherein the non-corrosive material is rigid, durable and provides a permeable upper surface that allows the passage of moisture as liquid or vapor while preventing the passage of solids to the flooring plenum space.

4. A method as defined in claim 3, wherein the flooring plenum ventilation system includes at least one reversible ventilation fan to complement and operate in coordination with standard poultry house ventilation systems to regulate flooring temperature, evacuate moisture and aid in ozone fumigation of a flooring plenum space.

5. A method as defined in claim 1, wherein said fumigating step includes a sufficient concentration of ozone for substantially eliminate pathogens, insects and fungi within the flooring plenum space of housing units.

\* \* \* \* \*